US009000248B2

(12) United States Patent
Takada

(10) Patent No.: US 9,000,248 B2
(45) Date of Patent: Apr. 7, 2015

(54) METHOD FOR MANUFACTURING OLEFINS

(75) Inventor: Shingo Takada, Wakayama (JP)

(73) Assignee: KAO Corporation, Tokyo (JP)

(*) Notice: Subject to any disclaimer, the term of this patent is extended or adjusted under 35 U.S.C. 154(b) by 123 days.

(21) Appl. No.: 13/504,662

(22) PCT Filed: Oct. 29, 2010

(86) PCT No.: PCT/JP2010/069314
§ 371 (c)(1),
(2), (4) Date: Apr. 27, 2012

(87) PCT Pub. No.: WO2011/052732
PCT Pub. Date: May 5, 2011

(65) Prior Publication Data
US 2012/0220808 A1 Aug. 30, 2012

(30) Foreign Application Priority Data
Oct. 30, 2009 (JP) ................... 2009-250630

(51) Int. Cl.
C07C 1/20 (2006.01)
B01J 35/00 (2006.01)
B01J 21/04 (2006.01)
B01J 27/18 (2006.01)
C07C 1/24 (2006.01)
C10G 3/00 (2006.01)

(52) U.S. Cl.
CPC .............. B01J 35/002 (2013.01); B01J 21/04 (2013.01); B01J 27/18 (2013.01); C07C 1/24 (2013.01); C07C 2521/04 (2013.01); C07C 2529/83 (2013.01); C10G 3/44 (2013.01); C10G 2400/22 (2013.01)

(58) Field of Classification Search
CPC .......... C07C 1/20; C07C 1/24; C07C 252/04; C07C 2529/83; B01J 21/04; B01J 35/002
See application file for complete search history.

(56) References Cited

U.S. PATENT DOCUMENTS

| 4,234,752 A * | 11/1980 | Wu et al. ................ 585/640 |
| 2004/0267073 A1 | 12/2004 | Zander et al. |
| 2007/0299291 A1 | 12/2007 | Koivusalmi |
| 2008/0027262 A1 | 1/2008 | Meudt et al. |
| 2008/0287722 A1 | 11/2008 | Dierker |
| 2011/0056656 A1 | 3/2011 | Ziehe et al. |

FOREIGN PATENT DOCUMENTS

| DE | 583 564 | 9/1933 |
| DE | 705 179 | 4/1941 |
| JP | 61 53230 | 3/1986 |
| JP | 9 157200 | 6/1997 |
| JP | 9-157200 | 6/1997 |
| JP | 2008 503453 | 2/2008 |
| WO | WO 01/44145 A1 | 6/2001 |
| WO | WO 2009/092349 A2 | 7/2009 |

OTHER PUBLICATIONS

Office Action issued Sep. 4, 2012, in Japanese Patent Application No. 2011-538501 with English translation.
Combined Chinese Office Action and Search Report issued Nov. 6, 2013, in Chinese Patent Application No. 201080048811.9 with English translation of category cited documents.
Edited by Catalysis Society of Japan, Shokubai Koza, vol. 8, Kogyo Shokubai Hanno I, 1$^{st}$ print, pp. 277-282, (1985).
Solomon, H.J., et al., "Catalysis of Alcohol and Ether Dehydration on Gamma—Alumina," I&EC Fundamentals, vol. 6, No. 3, pp. 325-333, (1967).
Bolder, F.H.A., et al., "Dehydration of alcohols in the presence of carbonyl compounds and carboxylic acids in a Fischer-Tropsch hydrocarbons matrix," Applied Catalysis A: General, vol. 300, pp. 36-40, (2006).
International Search Report Issued Nov. 30, 2010 in PCT/JP10/69314 Filed Oct. 29, 2010.
Extended European Search Report issued Jun. 2, 2014, in European Patent Application No. 10826862.4.
"168. Friedrich Asinger: Über Doppelbindungs—Isomerisierung bei der Herstellung von höhermolekularen aliphatischen geradkettigen Olefinen", Chemische Berichte, vol. 75, XP-055119321, Oct. 7, 1942 pp. 1247-1259.
Charles A. Walker, "Vapor-Phase Dehydration of Dodecanol over Alumina", Industrial and Engineering Chemistry, vol. 41, No. 11, XP-055119292, pp. 2640-2644.
V. I. Komarewsky, et al., "Catalytic Dehydration of 1-Hexanol and 1 Octanol", Journal of the American Chemical Society, vol. 67, XP-055119289, Apr. 1, 1945, pp. 557-558.

* cited by examiner

Primary Examiner — In Suk Bullock
Assistant Examiner — Sharon Pregler
(74) Attorney, Agent, or Firm — Oblon, McClelland, Maier & Neustadt, L.L.P.

(57) ABSTRACT

The present invention relates to a process for producing an olefin, including the step of subjecting an aliphatic primary alcohol having 12 to 24 carbon atoms to liquid phase dehydration reaction in the presence of a solid acid catalyst, wherein among a total acid content of the solid acid catalyst as measured by an ammonia temperature-programmed desorption ($NH_3$-TPD) method, an acid content of the solid acid catalyst as calculated from an amount of ammonia desorbed at a temperature not higher than 300° C. in the method is 70% or larger of the total acid content.

5 Claims, No Drawings

METHOD FOR MANUFACTURING OLEFINS

TECHNICAL FIELD

The present invention relates to a process for producing olefins, and more particularly, to a process for producing long-chain olefins by subjecting long-chain aliphatic primary alcohols to liquid phase dehydration reaction.

BACKGROUND ART

The process for producing olefin compounds by gas phase dehydration reaction of alcohols is already known. For example, Patent Document 1 discloses a process for producing olefin compounds in which a secondary alcohol is subjected to dehydration reaction in a gas phase at a temperature of from 300 to 400° C. in the presence of zirconium oxide.

However, in the gas phase reaction represented by the method described in Patent Document 1, it is required to vaporize all of raw materials used therein. In particular, when using a high-boiling alcohol as the raw material, energy consumption of the process tends to become excessively large, resulting in disadvantages from the viewpoint of costs. In addition, upon olefination of the alcohol under high-temperature conditions, branching of olefins owing to alkyl rearrangement and polymerization of the olefins also tend to occur in the olefination reaction, thereby causing the problems such as poor yield of the aimed reaction product.

On the other hand, there is also known the process for producing olefin compounds in which an alcohol is subjected to dehydration as a liquid phase reaction using a homogeneous acid catalyst such as concentrated sulfuric acid and sulfonic acid. Meanwhile, the "liquid phase reaction" as used herein means such a reaction which is carried out at a temperature not higher than a boiling point of the raw alcohol, i.e., not higher than the temperature at which a liquid phase of the alcohol is still present. For example, Patent Document 2 discloses a process for producing olefin compounds in which a primary alcohol is subjected to dehydration in a liquid phase using trifluoromethanesulfonic acid as a dehydration catalyst.

However, the homogeneous acid catalyst used in the liquid phase reaction represented by the method described in Patent Document 2 is generally corrosive and therefore tends to cause elution of metal components from a reactor. In addition, the liquid phase reaction needs neutralization of waste catalysts, etc., resulting in disadvantages in view of costs. Further, in the olefination using a catalyst having a strong acid site, similarly to the above reaction under high-temperature conditions, branching of olefins owing to alkyl rearrangement and polymerization of the olefins also tends to occur in the olefination reaction, thereby causing the problems such as poor yield of the aimed reaction product.

From the above reasons, it has been demanded to provide a method for producing olefins by subjecting alcohols to dehydration at a low temperature and in a liquid phase using a solid acid catalyst.

However, it is generally known that when the dehydration reaction of alcohols is conducted under low temperature conditions, intermolecular dehydration of the alcohols preferentially occurs to thereby produce an ether. For example, Patent Document 3 discloses a process for producing diisopropyl ether in which isopropyl alcohol is reacted at a temperature of from 150 to 300° C. using a sulfonic group-containing ion exchange resin as a catalyst.

Thus, in the dehydration reaction of alcohols, both intramolecular dehydration and intermolecular dehydration of the alcohols tend to occur in parallel. In particular, when the dehydration reaction of alcohols is conducted at a relatively low temperature, the intermolecular dehydration preferentially occurs to thereby produce an ether. In consequence, it is considered that olefins are hardly produced at a low temperature in an efficient manner.

CITATION LIST

Patent Literature

[Patent Document 1]: JP 61-53230 A
[Patent Document 2]: JP 2008-538206 A
[Patent Document 3]: JP 9-157200 A

SUMMARY OF INVENTION

Technical Problem

The present invention relates to a process for producing long-chain olefins with a high yield and a high selectivity by subjecting long-chain aliphatic primary alcohols to liquid phase dehydration reaction. Meanwhile, the "liquid phase reaction" as used herein means such a reaction which is conducted at a temperature not higher than a boiling point of the raw alcohol, i.e., not higher than the temperature at which a liquid phase of the alcohol is still present.

Solution to Problem

The present inventors have made the experiments in which long-chain aliphatic primary alcohols are subjected to liquid phase dehydration reaction at a relatively low temperature not higher than 280° C. in the presence of a solid acid catalyst having a low acid strength such as typically alumina and aluminum phosphate. As a result, it has been found that although a mixture containing an ether as a main component is produced in an initial stage of the reaction, when further continuing the reaction even after the raw alcohol is consumed, the ether unexpectedly undergoes decomposition to thereby produce olefins.

Thus, the present invention relates to a process for producing an olefin, including the step of subjecting an aliphatic primary alcohol having 12 to 24 carbon atoms to liquid phase dehydration reaction in the presence of a solid acid catalyst, wherein among a total acid content (a total amount of acid) of the solid acid catalyst as measured by an ammonia temperature-programmed desorption ($NH_3$-TPD) method, an acid content of the solid acid catalyst as calculated from an amount of ammonia desorbed at a temperature not higher than 300° C. in the method is 70% or larger of the total acid content.

Advantageous Effects of Invention

According to the process of the present invention, long-chain olefins can be produced with a high yield and a high selectivity by subjecting long-chain aliphatic primary alcohols to liquid phase dehydration reaction. In the process of the present invention, the dehydration reaction is carried out at a relatively low temperature in a liquid phase using the solid acid catalyst having a low acid strength. Therefore, the process can be performed with a less energy consumption, and branching of olefins owing to alkyl rearrangement and polymerization of the olefins hardly occur in the reaction.

DESCRIPTION OF EMBODIMENTS

[Raw Alcohol]

The alcohol used as a raw material in the present invention includes aliphatic primary alcohols having 12 to 24 carbon atoms. In view of conducting the liquid phase dehydration reaction at a temperature not higher than a boiling point of the raw alcohol in the process of the present invention, the number of carbon atoms contained in the raw alcohol is preferably from 12 to 20, more preferably from 14 to 20 and still more preferably from 16 to 20.

Specific examples of the raw alcohol include 1-dodecanol, 1-tridecanol, 1-tetradecanol, 1-pentadecanol, 1-hexadecanol, 1-heptadecanol, 1-octadecanol, 1-nonadecanol and 1-eicosanol.

These raw alcohols may be used alone or in combination of any two or more thereof

[Solid Acid Catalyst]

The solid acid catalyst used in the present invention exhibits such an acid content (an amount of acid) that among a total acid content of the solid acid catalyst as measured by an ammonia temperature-programmed desorption ($NH_3$-TPD) method, an acid content thereof as calculated from an amount of ammonia desorbed at a temperature not higher than 300° C. in the method (weak-acid content, or an amount of weak acid) is 70% or larger of the total acid content. Thus, the solid acid catalyst used in the present invention has a large proportion of the weak-acid content and therefore exhibits a low acid strength as a whole.

The ammonia temperature-programmed desorption method is such a method in which ammonia is adsorbed onto the solid acid catalyst, and then the catalyst is continuously heated while controlling the temperature rise rate to a predetermined value to measure an amount of ammonia desorbed from the catalyst as well as a temperature used upon the desorption. The ammonia adsorbed onto weak acid sites among whole acid sites of the solid acid catalyst tends to be desorbed at a low temperature, whereas the ammonia adsorbed onto strong acid sites among whole acid sites of the solid acid catalyst tends to be desorbed at a high temperature. Therefore, the acid content and the acid strength of the catalyst may be measured by the ammonia temperature-programmed desorption method. The measurement by the ammonia temperature-programmed desorption method may be performed, for example, using a catalyst analyzer "Full-Automatic Temperature-Programmed Desorption Apparatus TPD-1At" (tradename) available from Bel Japan, Inc. In the above TPD method, the amount of acid sites of the solid acid catalyst is determined as a relative amount based on 0.99 mmol/g as an amount of acid sites of ZSM-5 type zeolite "JRC-Z5-25H" (tradename) available from Exxon Mobil Catalyst, Inc., which is measured at a high peak (peak on a high-temperature side among two kinds of peaks observed). The peak is detected by quantitative determination of ammonia using a fragment m/e=17 of the ammonia in a mass spectrum.

The TPD (ammonia temperature-programmed desorption) may be measured by an ordinary measurement method generally used therefor. For example, the TPD measurement may be carried out after sequentially subjecting the solid acid catalyst to a pretreatment, an $NH_3$ adsorption treatment and a vacuum treatment under the following conditions.

Pretreatment: Temperature is raised up to 200° C. in helium over 20 min, and maintained at the same temperature for 1 h;

$NH_3$ adsorption treatment: $NH_3$ is adsorbed at 50° C. under 2.7 kPa for 10 min;

Vacuum treatment: Treated at 50° C. for 4 h; and

TPD measurement: While flowing a helium gas at a rate of 50 mL/min, temperature is raised up to 600° C. at a temperature rise rate of 5° C/min.

In the present invention, the weak-acid content of the solid acid catalyst is calculated from an amount of ammonia desorbed in a temperature range of from an initial temperature upon initiation of the measurement to 300° C. as a desorption temperature, whereas the strong-acid content (an amount of strong acid) thereof is calculated from an amount of ammonia desorbed in a temperature range exceeding 300° C. as the desorption temperature in which a whole amount of ammonia is desorbed from the solid acid catalyst. The total acid content of the solid acid catalyst is defined as a sum of the weak-acid content and the strong-acid content.

The proportion of the weak-acid content to the total acid content is calculated from the following formula:

Proportion (%) of weak-acid content =weak-acid content (mmol/g)/total acid content (mmol/g)×100.

The proportion of the weak-acid content of the solid acid catalyst is preferably 80% or larger, more preferably 90% or larger, still more preferably 93% or larger and further still more preferably 95% or larger. The upper limit of the proportion of the weak-acid content of the solid acid catalyst is preferably 100%. As the proportion of the weak-acid content of the solid acid catalyst becomes higher, it is possible to more effectively suppress occurrence of alkyl rearrangement and dimerization which tend to occur at strong acid sites of the solid acid catalyst and thereby enhance a yield of the olefins as an aimed product.

The weak-acid content of the solid acid catalyst preferably satisfies the above-specified proportion of the weak-acid content of the solid acid catalyst, and an absolute value of the weak-acid content is preferably 0.01 mmol/g or larger, more preferably 0.05 mmol/g or larger and still more preferably 0.1 mmol/g or larger.

The solid acid catalyst used in the present invention is not particularly limited, and any solid acid catalysts may be used as long as the proportion of a weak-acid content therein is 70% or larger. Specific examples of the suitable solid acid catalyst include alumina and aluminum phosphate.

The amount of the solid acid catalyst used in the reaction is not particularly limited. In the suspension bed reaction, from the viewpoints of a high reaction rate, the amount of the solid acid catalyst used therein is preferably from 0.1 to 200% by mass, more preferably from 0.5 to 100% by mass and still more preferably from 1 to 50% by mass on the basis of the raw alcohol. Since the process of the present invention is carried out at a relatively low temperature, no undesirable side reactions tend to occur even when the amount of the catalyst used therein is increased. Therefore, it is possible to appropriately control the reaction time by increasing or decreasing the amount of the catalyst used.

[Olefination Reaction]

The reaction used in the process of the present invention is a dehydration condensation reaction of the alcohol. Therefore, in the reaction, if water by-produced stays or remains in the reaction system, the reaction rate tends to be lowered. For this reason, from the viewpoint of enhancing the reaction rate, nitrogen is preferably introduced into the reaction system while stirring under a reduced pressure usually ranging from about 0.03 to about 0.09 MPa or under normal pressures to conduct the reaction while removing the water as produced out of the reaction system.

The reaction temperature is not higher than a boiling point of the raw alcohol from the viewpoints of attaining a high reaction rate and suppressing occurrence of undesirable side reactions such as alkyl rearrangement and polymerization of the olefins.

The reaction temperature is preferably from 160 to 300° C., more preferably from 200 to 290° C. and still more preferably from 240 to 280° C.

From the viewpoint of a high yield of the olefins as the aimed product, the reaction time may be controlled such that the conversion rate of the alcohol and the conversion rate of the ether as an intermediate reaction product are respectively preferably 95% or larger, more preferably 97% or larger, and still more preferably 98% or larger. Such a reaction time may vary depending upon the reaction temperature as well as the kind and amount of the solid acid catalyst used. In the suspension bed reaction, the reaction time is preferably from about 0.1 to about 20 h, more preferably from about 0.5 to about 10 hours and still more preferably from about 1 to about 5 hours.

Whereas, in the fixed bed reaction, LHSV (liquid hourly space velocity) is preferably from 0.1 to 5.0/h, more preferably from 0.2 to 3.5/h and still more preferably from 0.3 to 2.0/h.

In the process of the present invention, the alcohol is subjected to dehydration reaction at a relatively low temperature using the solid acid catalyst having a low acid strength, and therefore the intermolecular dehydration of the alcohol first occurs to thereby produce an ether. The conversion rate of the ether to olefins (olefination rate) tends to be very slow in the presence of the alcohol, and the ether is therefore produced with a high yield until the alcohol is almost completely converted into the ether. After the alcohol is completely consumed and converted into the ether, the olefination rate is considerably enhanced, so that the olefins can be efficiently produced.

Thus, in the process of the present invention, since the raw alcohol is once converted into the ether before producing the aimed olefins, a somewhat long reaction time is required. However, since the reaction is carried out at a low temperature using the solid acid catalyst having a low acid strength, there is such an advantage that branching of olefins owing to alkyl rearrangement and polymerization of the olefins hardly occur in the reaction. Further, since the dehydration reaction is conducted in a liquid phase, it is possible to reduce an amount of energy consumed in the reaction. In addition, since no undesirable side reactions occurs even when an amount of the catalyst used is increased, it is possible to solve the problem concerning the long reaction time by controlling the amount of the catalyst used.

According to the production process of the present invention, the conversion rate of the alcohol and the conversion rate of the ether as an intermediate reaction product reaches usually 80% or larger and preferably 90% or larger, and the yield of the olefins reaches usually 90% or larger. In addition, the rate of production of branched olefins and dimers of olefins contained in the resulting olefins are respectively usually 5% or smaller.

In the present invention, by separating the olefins solely from the resulting reaction product by distillative purification, it is possible to obtain olefins having a purity of 95% or higher.

The thus obtained olefins having a purity of 95% or higher are useful as a raw material or an intermediate raw material for organic solvents, softening agents, sizing agents, etc.

EXAMPLES

Example 1

A flask equipped with a stirrer was charged with 50.0 g (0.19 mol) of 1-octadecanol ("KALCOL 8098" (tradename) available from Kao Corp.; boiling point: 336° C.) and 1.5 g (3.0% by mass based on the raw alcohol) of γ-alumina (available from STREM Chemicals, Inc.) as a solid acid catalyst, and the contents of the flask were reacted under stirring while flowing nitrogen through the reaction system (nitrogen flow rate: 50 mL/min) at 280° C., for 5 hours. Meanwhile, the proportion of the weak-acid content of the above γ-alumina used as the solid acid catalyst was previously measured by an ammonia temperature-programmed desorption method using a catalyst analyzer "Full-Automatic Temperature-Programmed Desorption Apparatus TPD-1At" (tradename) available from Bel Japan, Inc., under the following conditions. As a result, it was confirmed that the proportion of the weak-acid content of the above γ-alumina was 92.5%.

<Measuring Conditions>

(Pretreatment)

The γ-alumina was accurately weighed in an amount of 0.10 g and placed in a cell for TPD measurement. Then, the γ-alumina was heated up to 200° C. in helium over 20 min, and maintained at the same temperature for 1 hour.

($NH_3$ Adsorption Treatment)

Using the thus pretreated γ-alumina, $NH_3$ was adsorbed thereon at 50° C. under 2.7 kPa for 10 min.

(Vacuum Treatment)

The γ-alumina obtained after the above $NH_3$ adsorption treatment was subjected to vacuum treatment in the cell for TPD measurement at 50° C. under $10^{-6}$ Pa for 4 hours to desorb ammonia physically adsorbed thereon.

(TPD Measurement)

The γ-alumina obtained after the above vacuum treatment was disposed in the above catalyst analyzer. While flowing helium through the catalyst analyzer at a rate of 50 mL/min, the temperature within the catalyst analyzer was raised up to 600° C. at a temperature rise rate of 5° C/min. The amount of acid sites of the γ-alumina was determined as a relative amount based on 0.99 mmol/g as an amount of acid sites of ZSM-5 type zeolite "JRC-Z5-25H" (tradename) available from Exxon Mobil Catalyst, Inc., which was measured at a high peak (peak on a high-temperature side among two kinds of peaks observed).

After completion of the reaction, the resulting reaction solution was diluted with hexane, and the resulting dilute solution was analyzed using a gas chromatographic analyzer "HP6890" (tradename) available from HEWLETT PACKARD Co., equipped with a column "Ultra ALLOY-1" (tradename; capillary column; 30.0 m×250 μm) available from Frontier Laboratories Ltd., and a detector (flame ionization detector (FID); injection temperature: 300° C.; detector temperature: 350° C. He flow rate: 4.6 mL/min) to conduct quantitative determination of the resulting reaction product.

As a result, it was confirmed that the conversion rate of the alcohol was 100%; the production rate of the ether was 0.1%; and the yield of whole olefins was 99.9%. Further, it was confirmed that among the whole olefins, the yield of branched olefins produced owing to the alkyl rearrangement was 0%; the yield of dimerized olefins was 1.6%; and the selectivity to the linear monomeric olefins (octadecenes) was 98.3%.

Meanwhile, the conversion rate of the alcohol, the production rate of the ether, the respective yields and the selectivity to the linear monomeric olefins were calculated according to the following formulae: Conversion Rate (%) of Alcohol=100-[amount of residual alcohol (mol)/amount of raw alcohol charged (mol)]×100, Production Rate (%) of Ether=[amount of ether produced (mol)×2/amount of raw alcohol charged (mol)]×100, Yield (%) of Whole Olefins=[{amount of branched olefins (mol)+amount of linear monomeric olefins (mol)+amount of dimerized olefins (mol)×2}/amount of raw alcohol charged (mol)]×100, Yield (%) of Branched Olefins=[amount of branched olefins (mol)/amount of raw alcohol charged (mol)]×100, Yield (%) of Dimerized Olefins=[amount of dimerized olefins (mol)×2/amount of raw alcohol charged (mol)]×100, and Selectivity (%) to linear monomeric olefins=[amount of linear monomeric olefins (mol)/amount of whole olefins (mol)]×100.

The reaction conditions and the results are shown together in Table 1.

Examples 2 to 6 and Comparative Examples 1 to 3

The reaction and measurement were carried out in the same manner as in Example 1 except that the reaction conditions were changed as shown in Table 1. The reaction conditions and the results are shown together in Tables 1 and 2.

TABLE 1

| | | Examples | | | | | |
|---|---|---|---|---|---|---|---|
| | | 1 | 2 | 3 | 4 | 5 | 6 |
| Catalyst | Kind | γ-Alumina | γ-Alumina | γ-Alumina | γ-Alumina | γ-Alumina | Aluminum phosphate |
| | Amount charged (% by mass) | 3 | 10 | 3 | 10 | 30 | 10 |
| | Proportion of weak-acid content (%) | 93 | 93 | 93 | 93 | 93 | 96 |
| | Weak-acid content (mmol/g) | 0.23 | 0.23 | 0.23 | 0.23 | 0.23 | 0.95 |
| Reaction temperature (° C.) | | 280 | 280 | 300 | 260 | 240 | 280 |
| Reaction time (h) | | 5 | 2 | 2 | 5 | 7.5 | 4 |
| Conversion rate of alcohol (%) | | 100.0 | 100.0 | 100.0 | 99.9 | 99.9 | 99.9 |
| Production rate of ether (%) | | 0.1 | 0.8 | 0.9 | 0.0 | 0.0 | 0.0 |
| Yield of whole olefins (%) | | 99.9 | 99.2 | 99.1 | 99.7 | 99.9 | 99.9 |
| Yield of branched olefins (%) | | 0.0 | 0.0 | 1.7 | 0.0 | 0.0 | 1.8 |
| Yield of dimerized olefins (%) | | 1.6 | 1.0 | 5.1 | 1.8 | 1.0 | 3.0 |
| Selectivity to linear monomeric olefins (%) | | 98.3 | 98.2 | 93.1 | 98.1 | 98.9 | 95.2 |

TABLE 2

| | | Comparative Examples | | |
|---|---|---|---|---|
| | | 1 | 2 | 3 |
| Catalyst | Kind | CP811 E-75 | CP811 E-75 | CBV720 |
| | Amount charged (% by mass) | 3 | 3 | 3 |
| | Proportion of weak-acid content (%) | 67 | 67 | 63 |
| | Weak-acid content (mmol/g) | 0.33 | 0.33 | 0.26 |
| Reaction temperature (° C.) | | 280 | 240 | 280 |
| Reaction time (h) | | 5 | 5 | 5 |
| Conversion rate of alcohol (%) | | 100.0 | 100.0 | 99.9 |
| Production rate of ether (%) | | 2.3 | 23.9 | 36.1 |
| Yield of whole olefins (%) | | 97.7 | 76.1 | 63.8 |
| Yield of branched olefins (%) | | 59.1 | 14.1 | 26.9 |
| Yield of dimerized olefins (%) | | 3.5 | 1.8 | 15.9 |
| Selectivity to linear monomeric olefins (%) | | 35.9 | 79.1 | 32.9 |

Note
CP811 E-75 (tradename; β-type zeolite available from Zeolyst International)
CBV720 (tradename; Y-type zeolite available from Zeolyst International)

In Comparative Example 1 in which the catalyst having a proportion of a weak-acid content of 67% was used, although the yield of the whole olefins was high, the olefins suffered from branching owing to alkyl rearrangement so that the yield of the branched olefins was as high as 59.1%. In addition, in Comparative Example 1, the olefins also suffered from dimerization so that the selectivity to the linear monomeric olefins (octadecenes) was as low as 35.9%.

In Comparative Example 2 in which the reaction temperature was lowered, although branching of the olefins owing to alkyl rearrangement and dimerization of the olefins were prevented from occurring as compared to Comparative Example 1, the production rate of the ether was as high as 23.9% and the yield of the olefins was low.

In addition, in Comparative Example 3 in which the catalyst having a proportion of a weak-acid content of 63% was used, the production rate of the ether was as high as 36.1%; the branching of the olefins owing alkyl rearrangement and the dimerization of the olefins were caused; and the selectivity to the linear monomeric olefins was as low as 32.9%.

Thus, in Comparative Examples 1 to 3, a large amount of the by-products were produced, and it was not possible to produce the aimed linear monomeric olefins with a high yield and a high selectivity.

On the other hand, in any of Examples 1 to 6, it was possible to produce the aimed linear monomeric olefins with a high yield and a high selectivity.

In particular, in Example 2 in which the amount of the catalyst used was increased as compared to that in Example 1, it was possible to enhance the reaction rate without loss of the yield owing to occurrence of side reactions.

Also, in Examples 3 to 5, it was confirmed that even though the reaction temperature was changed to 300° C., 260° C. and 240° C., respectively, the olefination reaction was allowed to proceed with a high efficiency.

In addition, in Example 6, it was confirmed that even though the catalyst used therein was changed to that having a proportion of a weak-acid content of 96%, the olefination reaction was allowed to proceed with a high selectivity and a high efficiency.

As apparently recognized from the above results, according to the process of the present invention, by subjecting long-chain aliphatic primary alcohols to liquid phase dehydration reaction, it is possible to produce long-chain olefins with a high yield and a high selectivity.

Industrial Applicability

In accordance with the present invention, olefins can be produced with a high yield and a high selectivity. The thus produced olefins are useful as direct raw materials or intermediate raw materials in extensive application fields including organic solvents, surfactants, oils for textiles, softening agents, cosmetics, drugs, lubricants, etc. More specifically, the olefins can be used in the form of creams, gels, lotions, solutions, emulsions or the like as components of hair cosmetics such as shampoos, rinses, treatments and conditioners, skin cosmetics, shower bath agents, etc.

The invention claimed is:

1. A process for producing an olefin, comprising subjecting an aliphatic primary alcohol having 12 to 24 carbon atoms to liquid phase dehydration reaction in the presence of a solid acid catalyst,
    wherein among a total acid content of the solid acid catalyst as measured by an ammonia temperature-programmed desorption ($NH_3$-TPD) method, an acid content of the solid acid catalyst as calculated from an amount of ammonia desorbed at a temperature not higher than 300° C. in the method is 70% or larger of the total acid content,
    wherein said liquid phase dehydration reaction is carried out at a temperature of from 160 to 290° C. and
    wherein the solid acid catalyst is alumina or aluminum phosphate.

2. The process for producing an olefin according to claim 1, wherein the aliphatic primary alcohol has 16 to 20 carbon atoms.

3. The process for producing an olefin according to claim 1, wherein the solid acid catalyst is used in an amount of from 1 to 50% by mass on the basis of the aliphatic primary alcohol.

4. The process for producing an olefin according to claim 3, wherein the aliphatic primary alcohol has 16 to 20 carbon atoms.

5. The process for producing an olefin according to claim 2, wherein the solid acid catalyst is used in an amount of from 1 to 50% by mass on the basis of the aliphatic primary alcohol.

* * * * *